(12) United States Patent
Wollenweber et al.

(10) Patent No.: US 6,403,529 B1
(45) Date of Patent: Jun. 11, 2002

(54) AQUEOUS, AGROCHEMICAL AGENTS CONTAINING ACTIVE INGREDIENTS

(75) Inventors: Horst-Werner Wollenweber, Duesseldorf; Ansgar Behler, Bottrop; Hans Christian Raths, Monheim; Hans-Georg Mainx, Leichlingen; Juergen Reinhardt, Hilden, all of (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/701,209

(22) PCT Filed: May 14, 1999

(86) PCT No.: PCT/EP99/03328

§ 371 (c)(1), (2), (4) Date: Jan. 29, 2001

(87) PCT Pub. No.: WO99/60851

PCT Pub. Date: Dec. 2, 1999

(30) Foreign Application Priority Data

May 26, 1998 (DE) .......................... 198 23 252

(51) Int. Cl.$^7$ .......................... A01N 3/02; A01N 37/00; A01N 25/00
(52) U.S. Cl. .......................... 504/116; 504/142; 424/405
(58) Field of Search .......................... 504/362, 116, 504/142; 424/405

(56) References Cited

U.S. PATENT DOCUMENTS

| | | | |
|---|---|---|---|
| 2,678,935 A | 5/1954 | Sundberg et al. | |
| 3,539,518 A | 11/1970 | Feighner et al. | |
| 4,022,808 A | 5/1977 | Yoshihara et al. | |
| 4,681,900 A | 7/1987 | Iwasaki | |
| 5,705,476 A | * 1/1998 | Hoffarth | ............ 510/535 |
| 6,103,770 A | 8/2000 | Trouve | |

FOREIGN PATENT DOCUMENTS

| | | |
|---|---|---|
| EP | 0 681 865 | 11/1995 |
| EP | 0 710 500 | 5/1996 |
| GB | 1 050 497 | 12/1966 |
| WO | WO 90/13533 | 11/1990 |
| WO | WO 91/15441 | 10/1991 |
| WO | WO 94/22301 | 10/1994 |
| WO | WO 96/22109 | 7/1996 |

OTHER PUBLICATIONS

Roempp, Lexikon, Chemie, 10$^{th}$ Edition 1997, p. 1764).

* cited by examiner

Primary Examiner—Alton Pryor
(74) Attorney, Agent, or Firm—John E. Drach; Steven J. Trzaska

(57) ABSTRACT

An aqueous agricultural composition containing: (a) at least one water-insoluble agrochemical; and (b) an additive corresponding to formula (I):

$$RO-(C_2H_4O)_n(C_3H_6O)_m-R' \quad (I)$$

wherein RO is an alcohol selected from the group consisting of branched or linear, saturated or unsaturated monohydric alcohols having from 1 to 6 carbon atoms or polyols having from 2 to 12 carbon atoms and from 2 to 6 hydroxyl groups, and R' is hydrogen or an ester group —CO—R" wherein R" is a branched or linear, saturated or unsaturated alkyl group having from 5 to 20 carbon atoms, m is a number from 1 to 10 and n is a number up to 40, and wherein the agrochemical and the additive are present in a ratio by weight of from 1:2 to 1:5.

16 Claims, No Drawings

AQUEOUS, AGROCHEMICAL AGENTS CONTAINING ACTIVE INGREDIENTS

The application is a 371 of PCT/EP99/03328 filed May. 14, 1999.

BACKGROUND OF THE INVENTION

This invention relates to water-based compositions which contain at least one agricultural chemical ("agrochemical") and certain alkoxylated fatty acids esters, to the use of such fatty acid esters for the production of compositions containing agrochemicals and to a process for applying agrochemicals to plants.

There are various known agents for protecting crops against pests and weeds. Unfortunately, they often show little or no solubility in water. Accordingly, these products are often marketed in the form of compositions based on mineral oils. On account of the environmental problems this involves and particularly on account of the inadequate biodegradability of the solvent, attempts are now being made to stop using these products. Instead, the agrochemicals are formulated as an aqueous dispersion or emulsion and may thus be readily be applied to the plants, for example by spraying.

Numerous auxiliaries are known to the expert for dispersing or emulsifying various active substances in water. In order to obtain stable dispersions or emulsions, however, very intensive shear forces often have to be applied in the production of the compositions. In addition, separation of the emulsion or dispersion can occur in the event of significant temperature differences during the storage and use of the compositions. In many cases, the plant protection compositions are also marketed as concentrates which are only diluted to the required extent in situ. In cases such as these, however, machines suitable for obtaining compositions in the required, stably emulsified form, such as high-speed mixers, are often not available.

Accordingly, WO 96/22109 describes the use of ethoxylated fatty acid esters having certain HLB values for the production of plant protection compositions or pharmaceutical preparations. These esters are biodegradable and self-emulsifying. However, plant protection compositions containing these esters as emulsifiers do not always have sufficient stability, particularly at high temperatures. Accordingly, there is still a need for water-based plant protection compositions which are stable in storage, even at high temperatures, and which are easy to produce.

It has surprisingly been found that compositions containing agrochemicals and certain propoxylated fatty acid ester as dispersants or emulsifiers satisfy the above-mentioned requirements in regard to stability and handling behavior.

BRIEF SUMMARY OF THE INVENTION

Accordingly, the present invention relates to water-based compositions containing water-insoluble agrochemicals and one or more compounds corresponding to general formula (I):

$$RO-(C_2H_4O)_n(C_3H_6O)_m-R' \qquad (I)$$

in which RO is an alcohol selected from the group of branched or linear, saturated or unsaturated monohydric alcohols containing 1 to 6 carbon atoms or polyols containing 2 to 12 carbon atoms and 2 to 6 hydroxyl groups and R' is hydrogen and/or a group —CO—R", where R" is a branched or linear, saturated or unsaturated alkyl group containing 5 to 29 carbon atoms, m is a number of 1 to 10 and n is 0 or a number of 1 to 40.

The compositions according to the invention may contain both solid and liquid water-insoluble ingredients. Accordingly, they form both dispersions and emulsions. In the present specification, dispersions and emulsions are collectively referred to as dispersions.

DETAILED DESCRIPTION OF THE INVENTION

The alkoxylated fatty acid esters corresponding to formula (I) are known substances which are described, for example, in U.S. Pat. No. 2,678,935, U.S. Pat. No. 3,539,518, U.S. Pat. No. 4,022,808 and GB 1,050,497, of which the disclosures are also part of the present application.

The alkoxylated fatty acid esters may be prepared by any methods known to the expert, for example by esterification of fatty acids with alkoxylated methanol, as described in U.S. Pat. No. 3,539,518. Unfortunately, this process has certain disadvantages, i.e. it comprises two steps, the esterification step takes a very long time and the products are colored by the high reaction temperatures. In addition, correspondingly produced fatty acids methyl ester ethoxylates have relatively high OH values after esterification which can be problematical for certain applications. Another method comprises directly reacting fatty acid esters with alkylene oxide in the presence of transition metal catalysts (cf. U.S. Pat. No. 4,022,808). However, the fatty acid alkyl ester alkoxylates are preferably produced by the heterogeneously catalyzed direct alkoxylation of fatty acid alkyl esters with ethylene oxide and/or propylene oxide on calcined or hydrophobicized hydrotalcites. This synthesis process is described in detail in WO 90/13533 and WO 91/15441, of which the disclosure is also part of the present application. The products obtained are distinguished by the low OH value, the reaction is carried out in a single stage and light-colored products are obtained. The fatty acid alkyl esters serving as starting materials may be obtained from natural oils and fats or may be synthesized.

The alkoxylated fatty acid esters contain at least 1 mole of propylene oxide groups per mole of ester. Compounds of formula (I) which contain between 1 and 10 moles of propylene oxide per mole of ester are preferred. In addition to the propylene oxide units, between 1 and 40 ethylene oxide groups are also preferably present in the molecule. Compounds corresponding to formula (I) containing between 1 and 30 moles of ethylene oxide per mole of ester are preferred. Both compounds which have been reacted with a mixture of ethylene oxide and propylene oxide and compounds which have been reacted with ethylene oxide and propylene oxide in two separate steps may be used as these mixed ethylene oxide/propylene oxide adducts. Where compounds of formula (I) which contain polyols as the alcohol component RO are used, the quantity data relating to the ethylene or propylene oxide units (indices n and m) are always based on the molecule as a whole. However, it is known that the exact distribution of the ethylene or propylene oxide units among the various hydroxyl groups obeys a distribution dependent on the synthesis.

The fatty acid esters —CO—R" contain alkyl groups R" with 5 to 29 carbon atoms. Suitable fatty acid components are natural and synthetic fatty acids, more particularly straight-chain, saturated or unsaturated $C_{6-30}$ fatty acids, including the technical mixtures thereof obtainable by lypolysis from animal and vegetable fats and oils, for example from coconut oil, palm kernel oil, soybean oil, sunflower oil, rapeseed oil, cottonseed oil, fish oil, bovine tallow and lard; special examples are caprylic acid, capric acid, lauric acid, lauroleic acid, myristic acid, myristoleic acid, palmitic acid, palmitoleic acid, oleic acid, elaidic acid, arachic acid, gadoleic acid, behenic acid and erucic acid.

The alcohol component RO may be selected from linear or branched, saturated or unsaturated monoalcohols containing 1 to 6 carbon atoms, for example methanol, ethanol, n- and i-propanol, n- and i-butanol, pentanol, hexanol, 2-ethylhexanol and cyclohexanol. Suitable polyols containing 2 to 6 carbon atoms are, for example, ethylene glycol, 1,2-propylene glycol, 1,2-butylene glycol, glycerol or trimethylol propane and pentaerythritol. Basically, all the hydroxyl groups of the alcohols are substituted by the alkoxides, although the terminal alkoxide groups are not all end-capped by ester groups. Accordingly, if polyols, such as glycerol or ethylene glycol, are used as the alcohol component RO, the compositions may contain compounds of formula (I) obtained by reaction of the full esters and also the partial esters with alkoxides. However, preferred compounds corresponding to formula (I) are those in which all the hydroxyl groups of the alcohols are alkoxylated and all terminal alkoxide groups are endcapped by ester groups with the formula —CO—R". Accordingly, in these preferred compounds, the substituent R" in formula (I) is exclusively a branched or linear, saturated or unsaturated alkyl group containing 5 to 29 carbon atoms.

In addition, alkoxylated fatty acid esters corresponding to formula (I) of which the fatty acid component is selected from linear unbranched $C_{6-18}$ fatty acids and of which the alcohol component is methanol, the esters of formula (I) preferably containing between 1 and 3 moles of propylene oxide and between 1 and 6 moles of ethylene oxide per mole of ester, are preferably used in the compositions according to the invention. Compounds such as these may be obtained, for example, by the above-described reactions of palmitic, stearic, oleic, linoleic or linolenic acid, lauric acid and myristic acid or esters thereof with alkoxides.

Also suitable are alkoxylated esters where the alcohol component is glycerol and the fatty acid component is selected from saturated or unsaturated, branched or unbranched fatty acids containing 18 to 22 carbon atoms and the esters contain between 3 and 10 moles of propylene oxide per mole of ester. Compounds of formula (I) additionally containing between 1 and 30 moles of ethylene oxide per mole of ester are particularly preferred. Compounds such as these may be obtained, for example, by reacting glycerol esters of natural fatty acids, such as for example palm oil, rapeseed oil or preferably castor oil, with ethylene oxide.

The compounds corresponding to formula (I) present in the compositions according to the invention are nonionic compounds which may be additionally characterized by their HLB value (hydrophilic-lipophilic balance as defined by Griffin, cf. Römpp, Lexikon Chemie, 10th Edition 1997, page 1764). Preferred compositions contain compounds of formula (I) with HLB values of 4 to 10 and, more particularly, 5 to 9.

The agrochemicals present in the compositions according to the invention are insoluble or only sparingly soluble in water at room temperature (21° C.). Sparingly soluble means that less than 10% by weight is soluble in water, more particularly less than 1% by weight. The agrochemicals may be solid or liquid at room temperature. In the context of the present invention, agrochemicals are understood to be substances suitable for plant protection and also herbicides and fertilizers. Plant protection agents also include insecticides, acaricides, nematicides and also repellents and rodenticides, sexual attractants, animal and bird deterrents and chemical sterilizers as described, for example, in Chemie der Pflanzenschutz- und Schädlingsbekämpfungsmittel, Vol. 1, Editor: R. Wegler, Springer Verlag Berlin, 1970. Depending on the agrochemical used, the compositions may have to be adjusted to a certain pH value optimal for the particular agrochemical.

The compositions contain at least one water-insoluble agrochemical, although mixtures of different agrochemicals may also be used. The compositions according to the invention may contain the agrochemical both in concentrated form, in which case they are formulated as concentrates containing more than 50% by weight to at most 90% by weight of agrochemical, and also in dilute form. Compositions containing between 0.1 and 10% by weight of agrochemicals, based on the weight of the composition, are preferred. The compositions according to the invention preferably have a water content of 10 to 90% by weight.

The dispersions according to the invention generally contain only small quantities —normally between 0.1 and 15% by weight—of compounds corresponding to formula (I). The quantity ratio between the compounds of formula (I) and the agrochemicals is preferably between 1:1 and 1:100. Particularly preferred compositions are characterized in that the ratio by weight between the compounds corresponding to formula (I) and the agrochemicals is in the range from 1:10 to 1:80 and more particularly in the range from 1:2 to 1:5.

Besides the agrochemicals and the compounds corresponding to formula (I), the water-based compositions according to the invention may contain other typical ingredients and additives, including solvents, such as ethylene and propylene glycols and $C_{1-6}$ alcohols, solid carrier materials, such as lignin, lignin derivatives or clays, and other known emulsifiers and dispersants. The dispersions may also additionally contain water-soluble agrochemicals. However, particularly preferred compositions are characterized in that they only contain emulsifiers corresponding to formula (I), i.e. no other emulsifiers or dispersants. The compositions according to the invention are stable in storage, even at temperatures above 30° C., and may be prepared without having to apply intensive shear forces, for example by manual stirring.

The present invention also relates to the use of compounds corresponding to formula (I) for the production of water-based compositions containing water-insoluble agrochemicals, at least one agrochemical being dispersed or emulsified in water together with compounds corresponding to formula (I).

The compositions according to the invention are formed without the application of intensive shear forces, for example simply by manual stirring. To this end, the compounds corresponding to formula (I) may be introduced first, for example in liquid form. The agrochemical is then added and the resulting mixture is dispersed in water. If compounds corresponding to formula (I) with melting points above room temperature are used, they may be used in molten form. However, compounds of formula (I) with a melting point below 25° C. are preferably used. It is also possible, however, initially to prepare a mixture of the agrochemical in water and then to emulsify or disperse the resulting mixture by addition of compounds corresponding to formula (I).

The present invention also relates to a process for treating plants with agrochemicals in which an aqueous dispersion as described in the foregoing is applied to plants in known manner, more particularly by spraying.

EXAMPLE

A water-based plant protection emulsion was prepared by mixing 50 g of the insecticide allethrin with the same quantity by weight of a rapeseed oil propoxylated with 3 moles propylene oxide and then ethoxylated with 30 moles ethylene oxide (by the method according to WO 90/13533) and emulsifying the resulting mixture with 900 g of tap water simply by stirring at room temperature. The emulsion thus obtained was stable in storage for more than 24 hours at 40° C.

What is claimed is:

1. An aqueous agricultural composition consisting essentially of:
    (a) at least one water-insoluble agrochemical; and
    (b) an additive corresponding to formula (I):

    RO—$(C_2H_4O)_n(C_3H_6O)_m$—R'     (I)

wherein RO is an alcohol selected from the group consisting of branched or linear, saturated or unsaturated monohydric alcohols having from 1 to 6 carbon atoms or polyols having from 2 to 12 carbon atoms and from 2 to 6 hydroxyl groups, and R' is hydrogen or an ester group —CO—R" wherein R" is a branched or linear, saturated or unsaturated alkyl group having from 5 to 29 carbon atoms, m is a number from 1 to 10 and n is a number up to 40, and wherein the agrochemical and the additive are present in a ratio by weight of from 1:2 to 1:5.

2. The composition of claim 1 wherein in formula I RO is a glycerol residue and R" is a branched or linear, saturated or unsaturated alkyl group having from 17 to 29 carbon atoms.

3. The composition of claim 1 wherein in formula I m is a number from 1 to 6 and n is a number from 1 to 30.

4. The composition of claim 1 wherein in formula I m is a number from 1 to 3 and n is a number from 1 to 6.

5. The composition of claim 1 wherein in formula I —CO—R" is a ricinoleic acid residue and RO is a glycerol residue.

6. The composition of claim 1 wherein in formula I RO is a methanol residue and R" is a branched or linear, saturated or unsaturated alkyl group having from 5 to 17 carbon atoms.

7. The composition of claim 1 wherein the agrochemical is present in the composition in an amount of from 0.1 to 10% by weight, based on the weight of the composition.

8. The composition of claim 1 wherein the additive of formula I has an HLB value of from 4 to 10.

9. The process of claim 1 wherein the additive of formula I has an HLB value of from 4 to 10.

10. A process for treating plants comprising contacting the plants with a composition consisting essentially of:
    (a) at least one water-insoluble agrochemical; and
    (b) an additive corresponding to formula (I):

    RO—$(C_2H_4O)_n(C_3H_6O)_m$—R'     (I)

wherein RO is an alcohol selected from the group consisting of branched or linear, saturated or unsaturated monohydric alcohols having from 1 to 6 carbon atoms or polyols having from 2 to 12 carbon atoms and from 2 to 6 hydroxyl groups, and R' is hydrogen or an ester group —CO—R" wherein R" is a branched or linear, saturated or unsaturated alkyl group having from 5 to 29 carbon atoms, m is a number from 1 to 10 and n is a number up to 40, and wherein the agrochemical and the additive are present in a ratio by weight of from 1:2 to 1:5.

11. The process of claim 10 wherein in formula I RO is a glycerol residue and R" is a branched or linear, saturated or unsaturated alkyl group having from 17 to 29 carbon atoms.

12. The process of claim 10 wherein in formula I m is a number from 1 to 6 and n is a number from 1 to 30.

13. The process of claim 10 wherein in formula I m is a number from 1 to 3 and n is a number from 1 to 6.

14. The process of claim 10 wherein in formula I —CO—R" is a ricinoleic acid residue and RO is a glycerol residue.

15. The process of claim 10 wherein in formula I RO is a methanol residue and R" is a branched or linear, saturated or unsaturated alkyl group having from 5 to 17 carbon atoms.

16. The process of claim 10 wherein the agrochemical is present in the composition in an amount of from 0.1 to 10% by weight, based on the weight of the composition.

\* \* \* \* \*